(12) United States Patent
Carlsson

(10) Patent No.: US 7,947,223 B2
(45) Date of Patent: May 24, 2011

(54) BIOSENSOR APPARATUS FOR DETECTION OF THERMAL FLOW

(75) Inventor: Thomas Carlsson, Uppsala (SE)

(73) Assignee: Senzime AB, Uppsala (SE)

(*) Notice: Subject to any disclaimer, the term of this patent is extended or adjusted under 35 U.S.C. 154(b) by 301 days.

(21) Appl. No.: 12/092,081

(22) PCT Filed: Oct. 31, 2006

(86) PCT No.: PCT/SE2006/050442
§ 371 (c)(1),
(2), (4) Date: Sep. 20, 2008

(87) PCT Pub. No.: WO2007/053105
PCT Pub. Date: May 10, 2007

(65) Prior Publication Data
US 2009/0098019 A1    Apr. 16, 2009

(30) Foreign Application Priority Data

Oct. 31, 2005 (SE) ...................................... 0502413

(51) Int. Cl.
*G01N 25/20* (2006.01)
(52) U.S. Cl. ......... 422/51; 422/68.1; 422/82.12; 374/31
(58) Field of Classification Search ............ 422/68.1, 422/51, 82.12; 374/31–42
See application file for complete search history.

(56) References Cited

U.S. PATENT DOCUMENTS

| | | | |
|---|---|---|---|
| 4,492,480 A | 1/1985 | Wadso et al. | |
| 5,018,872 A * | 5/1991 | Suszynski et al. | 374/133 |
| 5,707,149 A | 1/1998 | Freire et al. | |
| 5,790,752 A * | 8/1998 | Anglin et al. | 392/483 |
| 2002/0045246 A1 * | 4/2002 | McMillan et al. | 435/306.1 |
| 2002/0075551 A1 * | 6/2002 | Daneman et al. | 359/254 |
| 2004/0028112 A1 * | 2/2004 | Carlsson et al. | 374/36 |
| 2005/0221373 A1 * | 10/2005 | Enzelberger et al. | 435/6 |
| 2005/0250199 A1 * | 11/2005 | Anderson et al. | 435/287.2 |

FOREIGN PATENT DOCUMENTS

| | | |
|---|---|---|
| WO | 95/14962 A1 | 6/1995 |
| WO | 98/50147 A1 | 11/1998 |

* cited by examiner

*Primary Examiner* — In Suk Bullock
*Assistant Examiner* — Timothy G Kingan
(74) *Attorney, Agent, or Firm* — Young & Thompson

(57) ABSTRACT

In general terms the biosensor apparatus according to the invention comprises a housing (5, 6), a pair of heat sinks (11, 12) and a pair of heat reflectors (13, 14) thermally floating relative to the heat sinks, and a pair of Peltier elements (16) attached to and in thermal contact with the heat sinks (11, 12), one element (16) on each heat sink (11, 12). The housing is made of an insulating material, and the heat sinks (11, 12) are made of a material with thermal properties large enough to absorb the heat flow with only a very slight, negligible disturbance in its temperature, to render their envelope surface having a high heat emissivity. The heat reflectors (13, 14) are made of a material having a very low emissivity and have a generally flat and thin disc shaped structure and acts primarily as radiation shields.

17 Claims, 7 Drawing Sheets

BIOSENSOR APPARATUS FOR DETECTION OF THERMAL FLOW

The present invention relates to biosensor systems in general, and in particular to a thermal flow transducer type of system, especially for enzymatic serial reactions.

BACKGROUND OF THE INVENTION

The term biosensor is commonly referred to as a measuring device that combines a biological sensing part in close proximity to a non-biological transducer which converts the biochemical information produced in the biological part into a measurable signal.

The most commonly employed transducer in current biosensor instruments (e.g. a clinical analyser) is electrochemically based. The analyser is often used in connection with a biosensor unit (one-time use), which before operation, is connected to the analyser. The biosensor unit contains both the biological and the electronic part. It has turned out that there is a significant cost of designing and fabricating a custom integrated biosensor unit that includes both the biological sensing part and the necessary electronic elements. One major reason for this is that the materials and methods used for electronic components require very high temperatures, which temperature levels are incompatible with the fabrication of the biological part. It has turned out to be difficult to combine these contradicting demands of the devices to be manufactured. In a recently invented biosensor technology (disclosed in EP application 01952081.6) thermal flow has been used as transducer, circumventing the above mentioned drawbacks with electrochemical detection. However, it has turned out that this transducer technology could have a drawback of being sensitive, in some cases, to interference from rapid and sudden temperature and heat radiation changes in the environment and therefore making it less useful in these cases.

SUMMARY OF THE INVENTION

In order to eliminate the drawbacks associated with the prior art device and to eliminate the need of using thermostatting, a novel bio sensor apparatus is provided comprising a housing made of an insulating material in conjunction with the specially designed heat sinks and heat reflectors. When the analysis is to be carried out the biosensor unit itself is easily connected and brought in thermal contact with the transducer unit in the instrument.

Thereby, only the requirements and limitations set by the biological system need to be considered in the manufacturing process of the biosensor unit. Also, packaging of the biosensor unit should thereby be simplified.

The biosensor apparatus according to the present invention is defined in claim 1.

In a preferred embodiment it comprises a housing; a holder, a pair of heat sinks and a pair of heat reflectors, thermally floating relative to the heat sinks suspended in said holder and thermally floating relative to the environment inside the holder and housing, and arranged with their surfaces facing each other; and a pair of Peltier elements thermally attached to said heat sinks, one element on each heat sink, on said facing surfaces, forming a gap between them for the accommodation of a generally flat biosensor unit.

The term "generally flat" as used hereinafter indicates that at least the reaction chamber of such a biosensor unit should be flat in the meaning that the thickness of such a chamber and the opposite large walls enclosing it is substantially smaller than the dimensions of said large walls. The transducer unit as well as the biosensor unit shall be designed so as to enable a continuous flow of a sample of bio fluid through the reaction chamber. Therefore, the transducer unit as well as the biosensor unit comprises suitable channels for this purpose. Heat produced by the reaction between substrates in the fluid and enzymes is transmitted via the opposite large walls of the chamber to the respective Peltier element, thereby making it possible to measure the concentration of the substrate.

Preferably, the Peltier elements are arranged so as to be in a heat conducting contact with thin foils defining opposite walls of a reaction chamber defined by the biosensor unit when the biosensor unit is in an operative position between the Peltier elements. Inside the reaction chamber, enzymes adapted for the reaction are arranged. A basic principle of the apparatus is that the heat transmitting area between Peltier elements and reaction chamber walls should be as large as possible in relation to the volume of the reaction chamber. Therefore, the thickness of the reaction chamber is small in relation to the dimensions of the walls defined by the foils.

For best performance of the biosensor apparatus the heat conducting contact area between Peltier elements and the foils should correspond to the total reaction chamber wall area defined by said foils. Total chamber wall area is referred to as the total area of the outer surface of the chamber wall-forming part of the foils directed towards the respective Peltier element.

According to a preferred embodiment at least one of the Peltier elements is movable to and from the other Peltier element in order to facilitate insertion of the biosensor unit between the Peltier elements.

The housing comprises two thermally insulating blocks providing a generally constant air temperature around the heat sinks, the reflectors, the holder and the Peltier elements during operation. The insulating blocks are preferably made of a material which has a low thermal conductivity in combination with high resistance against heat radiation selected from polyurethane foam, expanded polystyrene etc.

The holder is made up of two plates suspended in said housing. The plates are preferably made of a material with a low thermal conductivity such as polymethylmethacrylate.

At least one of the heat sinks should be moveable in relation to one of the plates. In one embodiment of the invention, the housing is defined by two opposite blocks made of a thermally insulating material having low thermal conductivity and low absorption of heat radiation and a holder located between said opposing blocks, each reflector being connected to a respective one of the holders. The holder accommodates the two heat sink/Peltier element units and the reflectors as well as the biosensor unit.

The invention also relates to a biosensor unit, defined in claim 9.

Further features and advantages of the invention are presented in the following detailed description of preferred embodiments and in the annexed patent claims.

BRIEF DESCRIPTION OF THE DRAWINGS

FIG. 3b illustrates the body with the reaction chamber covered with a thin foil, seen from opposite direction in relation to FIG. 3a.

DETAILED DESCRIPTION OF PREFERRED EMBODIMENTS OF THE INVENTION

Figure 1:
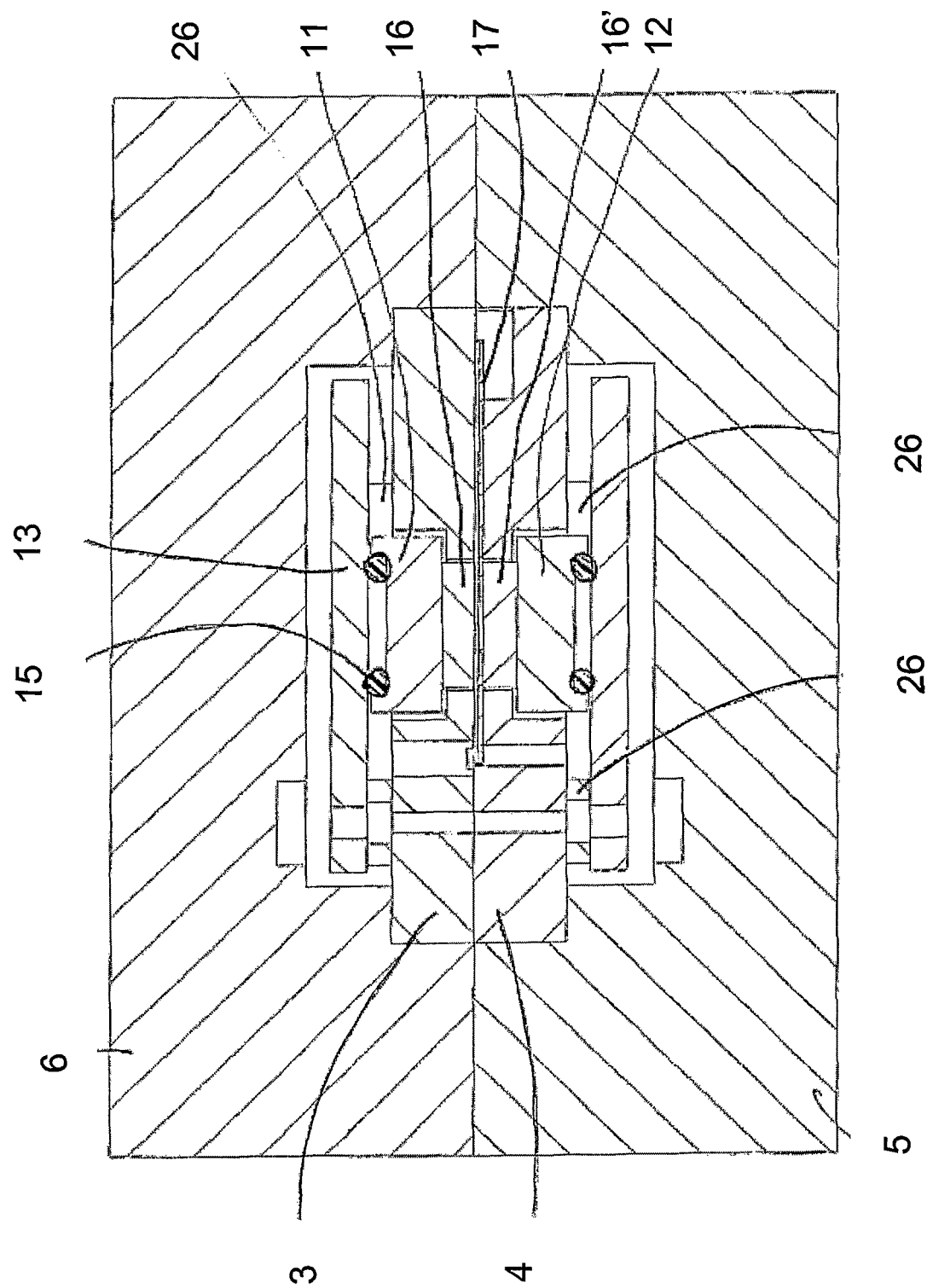
FIG. 1 illustrates a biosensor apparatus according to the invention in cross-section.

In FIG. 1 the apparatus according to the invention is shown in a cross-sectional view.

In general terms the biosensor apparatus according to the invention comprises a housing consisting of two housing blocks, a first housing block 5, and a second housing block 6. These two blocks are made of a thermally insulating material, i.e. having low thermal conductivity in assembled state they form an inner compartment housing the active devices, i.e. a transducer unit and a biosensor unit comprising a reaction chamber, and generally indicated with reference numeral 2 in FIG. 2 (to be further described below with reference to FIGS. 2a-2c). In the reaction chamber reactions generating heat can be performed. There are two heat sinks 11, 12 made of a material with heat capacity and heat diffusivity large enough to absorb and dissipate the heat flow from the enzymatic reaction quickly with only a slight, negligible disturbance in the temperature of the inner compartment, to render their envelope surface having a high heat emissivity. Suitably the thermal properties are selected such that absorption of a heat flow from a reaction in said biosensor unit is enabled within a time of 5-30 seconds, preferably 10-20 seconds, and thereafter the absorbed heat is released within a time less than 2 min, preferably less than 1 min, more preferably less than 40 seconds, most preferably less than 20 seconds.

The heat reflectors 13, 14 are made of a material having a surface with very low emissivity and have a generally flat and thin disc shaped structure and acts primarily as radiation shields. They float thermally relative to the heat sinks, said heat sinks 11,12 being arranged in said housing 5, 6 and thermally floating relative to the environment inside the housing 5, 6, and a pair of Peltier elements 16 attached to and in thermal contact with said heat sinks 11, 12, one element 16 on each heat sink 11, 12. There is a gap between them for the accommodation of a generally flat biosensor unit 17.

The housing is suitably generally cylindrical, which is practical from a design point of view. Also from a thermal point of view a circular configuration is preferred since heat gradients will be more favorable. However, any geometry that would suit a specific purpose is equally possible.

Figure 2A:
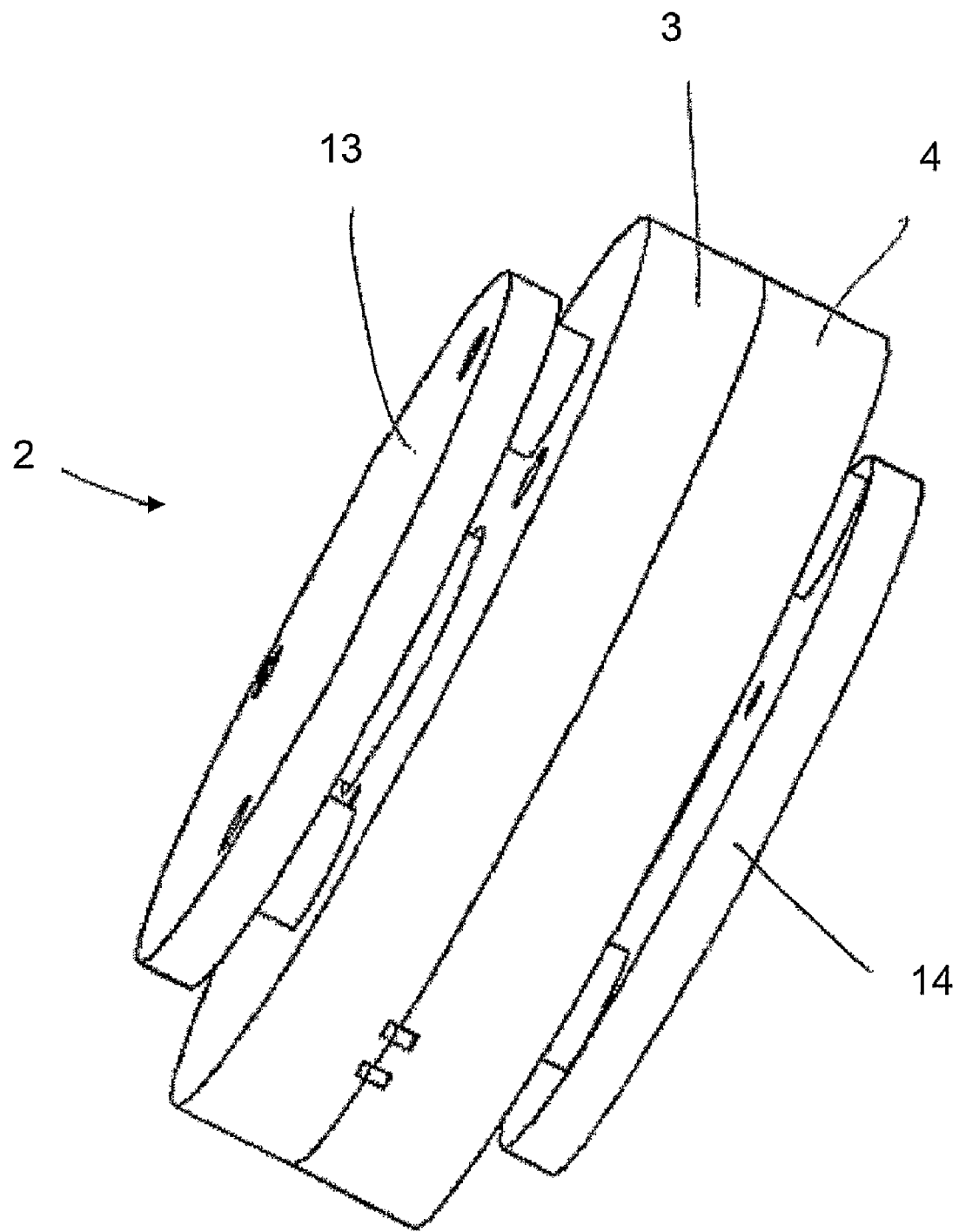
FIG. 2*a* is a view, showing a biosensor apparatus according to the present invention without the housing.
Figure 2B:
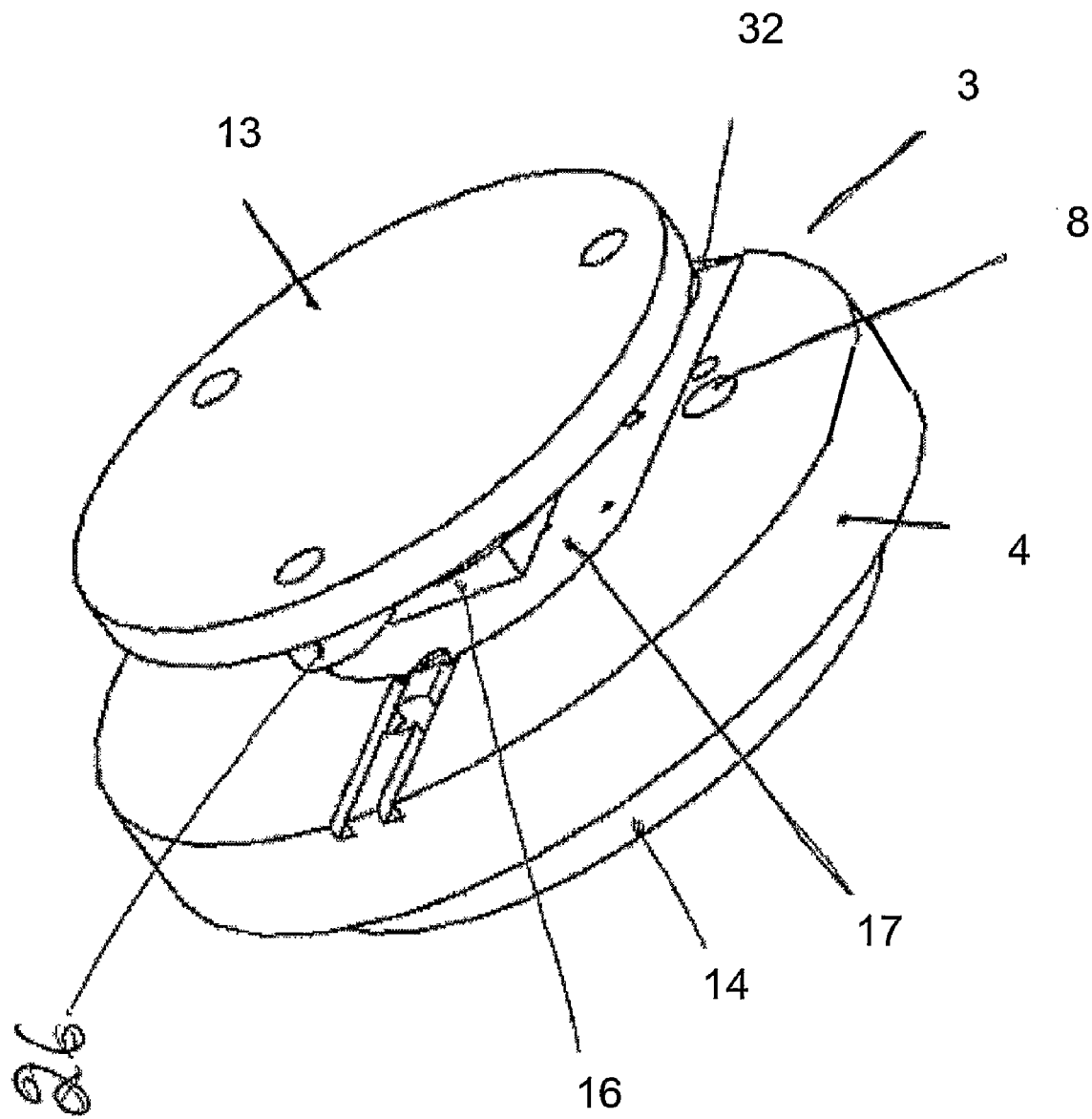
FIG. 2*b* shows the apparatus with one of the holder plates taken away.
Figure 2C:
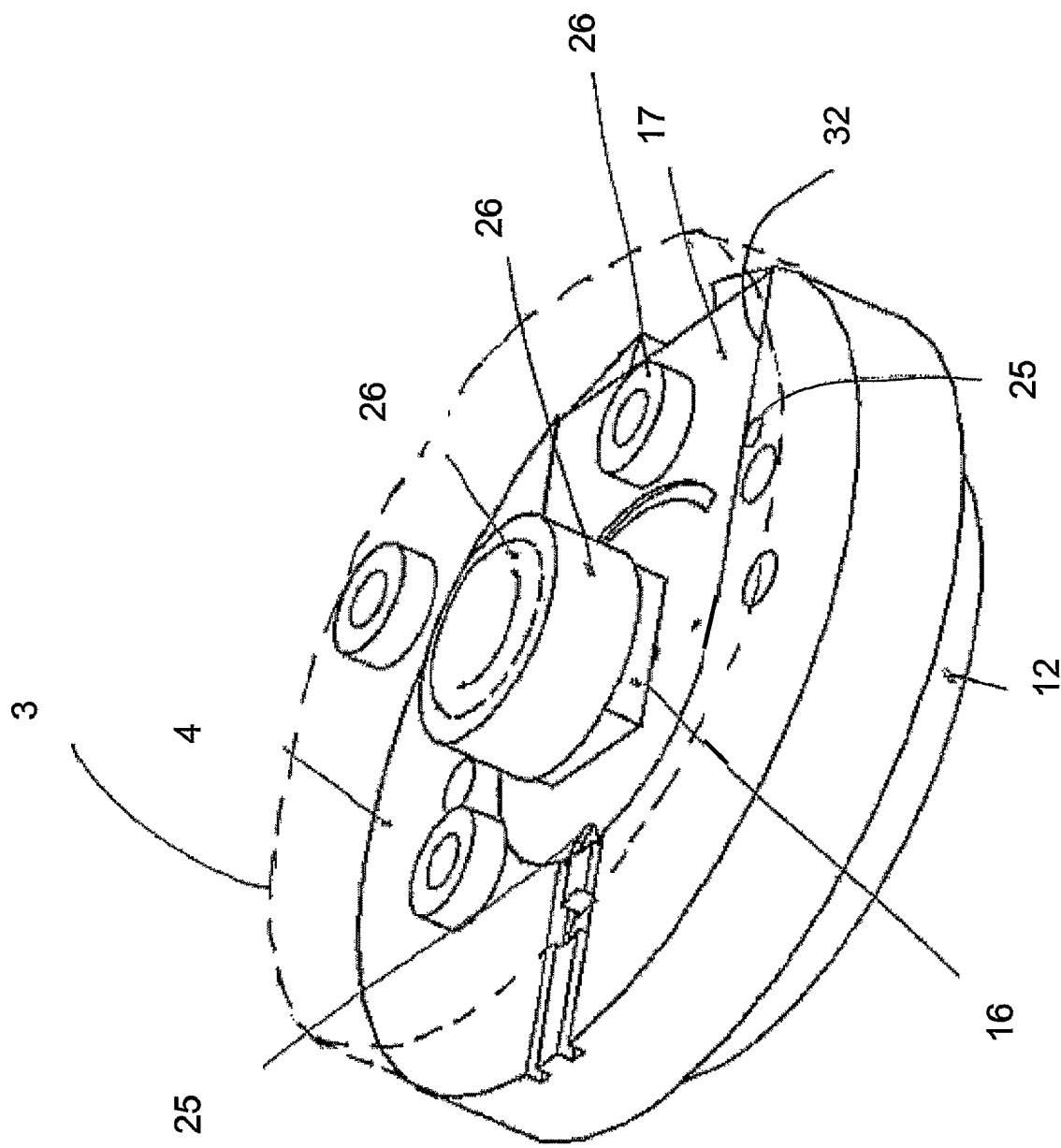
FIG. 2*c* shows the apparatus in the same view as in FIG. 2*b*, but with one reflector taken away.

Thus, the active part of the biosensor apparatus according to the invention is further illustrated in FIGS. 2a-c (perspective views with parts broken away; elements common to the figures are given the same reference numerals) and is generally indicated with reference numeral 2. It comprises a holder, formed from, or defined by, two opposing plates 3, 4 where the plate 3 is axially moveable a short distance in relation to plate 4 which is fixed to the first housing block (not shown). The two plates 3, 4 are provided with holes 8 for the accommodation of holding pins (see FIG. 2b). The plates and pins are made of a material with low heat conductivity, preferably synthetic polymer (plastics). The fixed plate 4 is provided with a depression 32 adapted to receive the flat and thin biosensor unit 17 in a close fit. Onto the plates 3, 4, the two heat sinks 11, 12 and reflectors 13,14 are placed. The heat sinks 11, 12 are slightly moveable in relation to plates 3 and 4 and to the reflectors, whereas the said reflectors are fixed to plate 3 and 4, respectively, by means of spacer members 26. The heat sinks are rendered movable by the provision of O-rings 15 of an elastic material, such that the compressibility of the O-ring will enable some degree of movement.

The heat sinks 11, 12 are made of a material with certain heat diffusivity and heat capacity sufficient enough to absorb the heat flow with only a slight, negligible disturbance in its temperature and surrounding. Examples of such materials are e.g. aluminium and copper. The heat sinks are preferably designed so as to just cover the surface of the Peltier elements, and having a generally cylindrical configuration. Thereby, their envelope surface, i.e. the circular surface perimeter, should have a high heat emissivity, in order to provide for rapid and even radiation of heat.

The reflectors 13, 14 are made of a material having a surface with high heat reflectivity (low emissivity), such as e.g. polished aluminium, and with a generally flat, circular, thin structure (disc shaped). The facing area of said disc should be 1-10 times larger, preferably 3-9 times larger than the facing area of the heat sink. In one prototype embodiment it is 8 times larger than the facing area of the heat sink.

On each heat sink there is mounted a Peltier element 16, 16' in very good thermal contact with the heat sink. The Peltier elements are attached to the heat sinks such that they face each other. The heat sinks are to some extent movable in relation to the reflectors through the compressibility of the O-ring 15.

Thus, the heat sinks 11, 12 are arranged so as to form a space between them and each corresponding reflector 13, 14 by said separating, insulating and compressible O-ring 15 made of a material with low thermal conductivity, preferably plastics. Furthermore, the heat sinks and reflectors are arranged in such a way that they "thermally float" with respect to each other and with respect to the holder, by the provision of spacers 26, made of a material having low thermal conductivity, and by said O-ring 15. There is also provided an insulating air gap of about 1 mm surrounding the heat sinks and reflectors.

The expression "thermally floating" should be taken to mean that the heat exchange between the heat sinks and the reflectors on one hand, and between the heat sinks and the holder/housing assembly on the other hand is kept minimal.

Figure 3A:
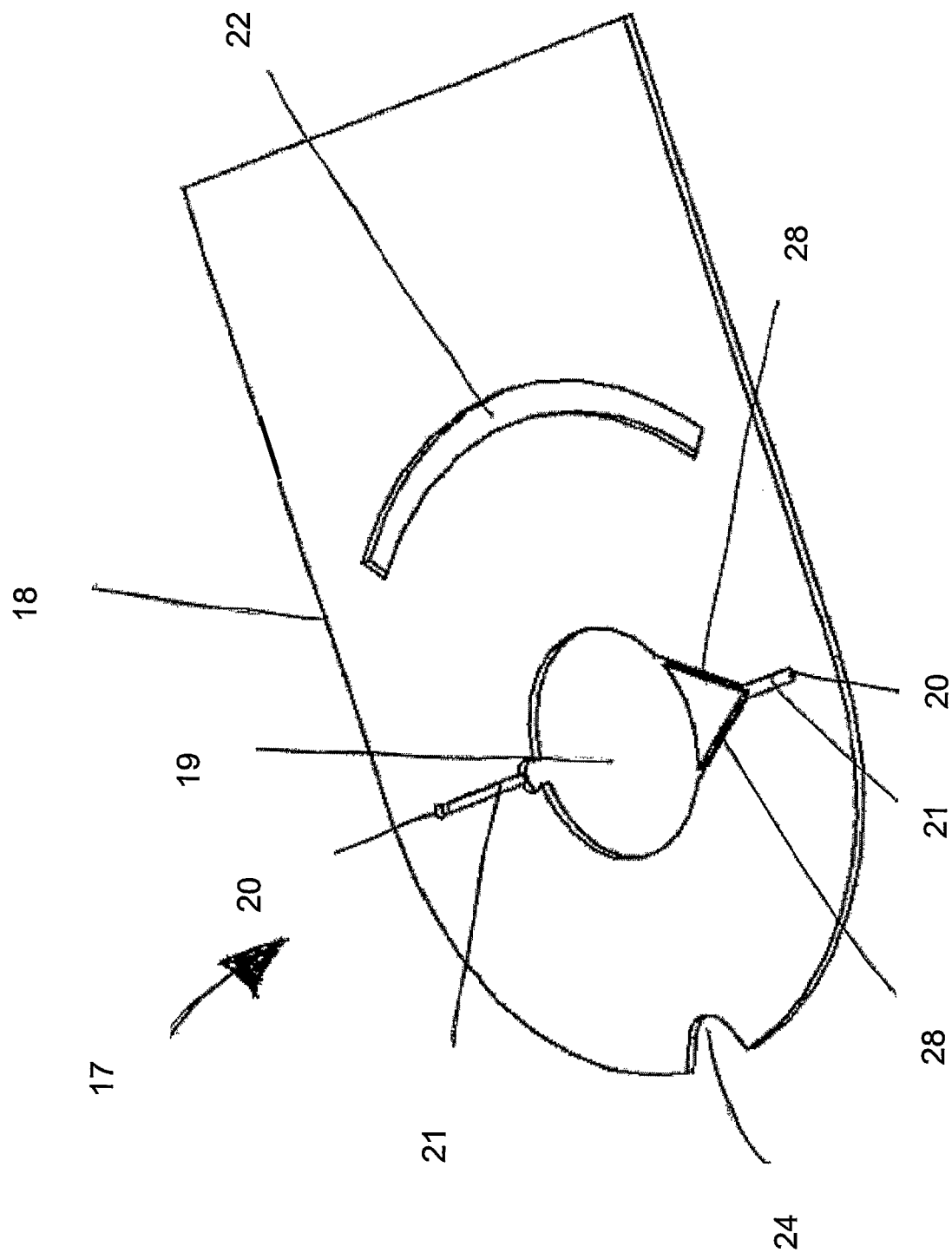
FIG. 3a shows a body of the biosensor unit with a reaction chamber open.

The biosensor unit 17 shown in FIG. 3a to be used with the apparatus comprises a generally flat body 18, comprising a number of features. An essentially circular opening 19 in the body 18 forms a reaction chamber.

Figure 3B:
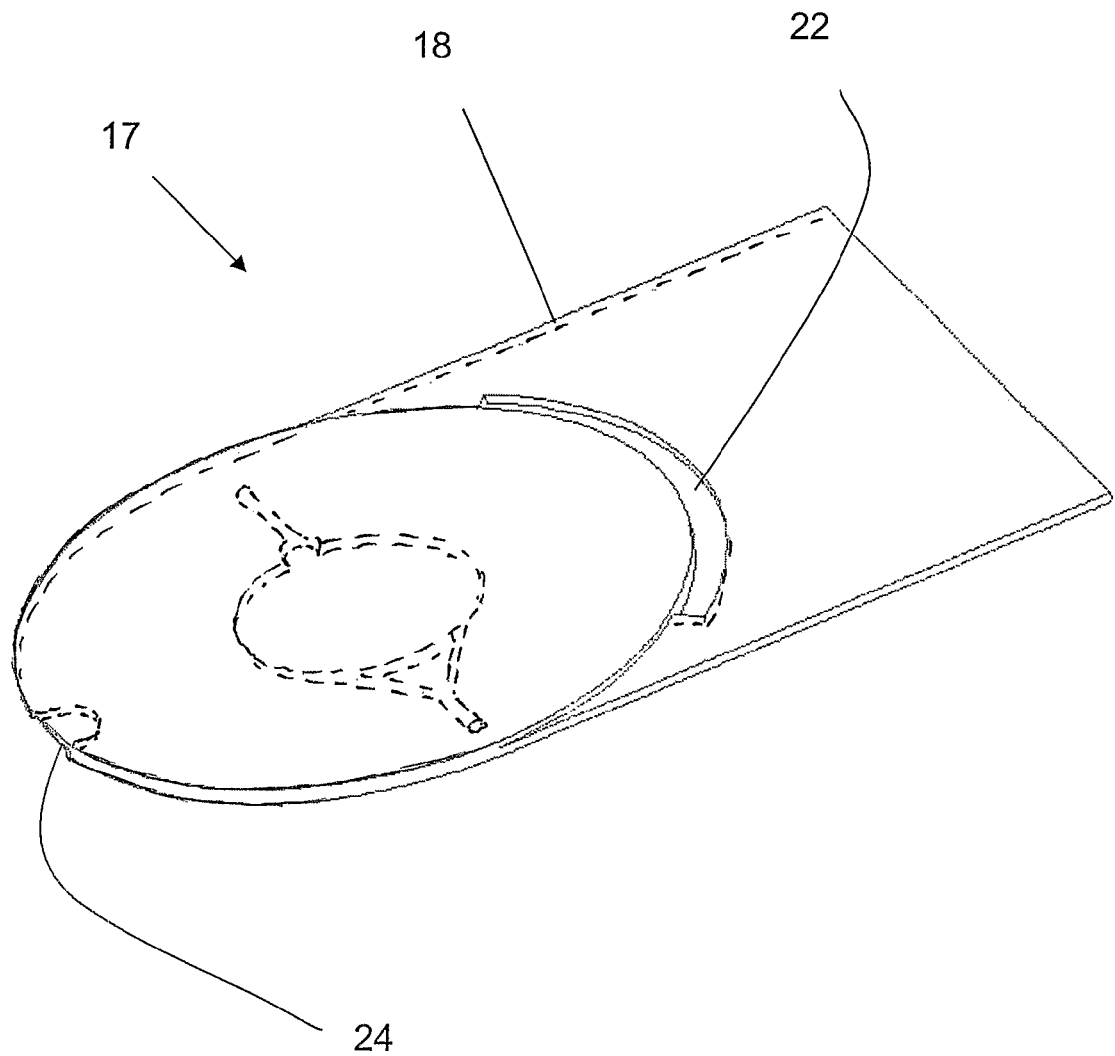
Figure 4:
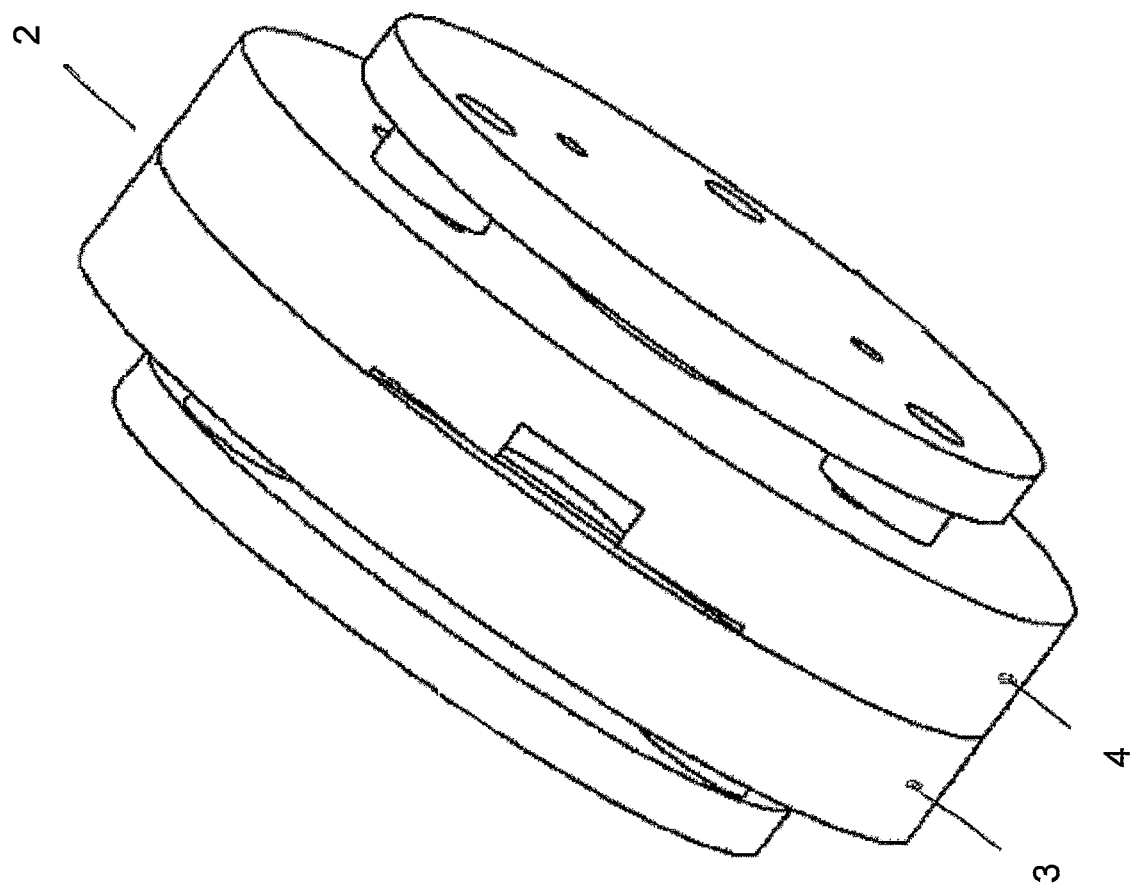
FIG. 4 is a view of the complete body with the two plates together with the heat sinks/Peltier elements and reflectors attached.

The reaction chamber 19 is formed by covering the opening 19 on each side by a thin foil 23 (see FIG. 3b) made of a polymeric material, e.g. a polyimide. This polymer is very strong and can thus be made very thin, yielding a very high rate of heat conduction through it, which is essential for the invention. Between the foils 23 there can be provided support materials to form a "bed", on which e.g. an enzyme can be immobilized by methods known in the art. The "bed" in the reaction chamber should preferably have a low heat capacity and the bordering edge (circumferential wall) in the reaction chamber facing into the reaction chamber, should have a low thermal conductivity. Suitable bed materials are porous glass, silicon, polymers etc. The distance between the surfaces should be as small as possible, and the lower limit is only set by manufacturing/technological limitations. A practical upper limit for the thickness of the active matrix in the reaction chamber is probably about 1 mm.

Thus, in operation the reaction chamber is an integral part of the body 18. Inlet and outlet of fluid flow is achieved through two openings 20 in the holder 18 and fluid channels 21 in the form of grooves in the surface of the body 18, providing a fluid communication means between openings 20, preferably located diametrically opposite each other, and reaction chamber 19. On the inlet side there are provided two channels 28, branching from the inlet channel 21 for improving the distribution of the flow and ascertaining a uniform passage of fluid from the inlet to the outlet.

In order to minimize the conduction of heat through the body 18, it is provided with slit 22 forming an insulating air gap. The body has a cut-out portion 24 serving a function to be described below.

In this application there is disclosed one example of a biosensor unit design. The overall detailed design of the biosensor unit with body, reaction chamber and fluid channels is a matter of construction based on which type of specific reaction it is to be applied for. The example shown here is approximately 30×20×0.5 mm, but the appropriate dimensions and overall design should be optimized for each special case.

The biosensor unit is preferably made of an insulating material, such as a polymeric material, or other materials such as silicon, that can be easily processed to the desired structure.

The thickness of the reaction chamber 19 (from one external surface to another) corresponds closely to the distance between the opposing Peltier elements, for reasons to be discussed below.

Referring now to FIG. 2c, the apparatus according to the invention is operated as follows.

By virtue of the heat sink/Peltier element aggregate being attached to the moveable plate 3 (shown in phantom lines for clarity), it can easily be moved such that the gap between the Peltier elements 16 is slightly widened. Thereby it will be an easy matter to insert the biosensor unit 17 between them. When the biosensor unit has been inserted to an extent that the cut-out portion 24 of the biosensor unit 17 and a pin (not shown) in hole 25 meet, the biosensor unit will be "snap-fitted" in position. Cut-out portion 24 and pin thereby define snap fitting members. When the biosensor unit is in its position in the recess 32 in plate 4, and the plate 3 is moved to its inner position (by the movement of block 6 in contact with block 5), the heat sink/Peltier element aggregates, by action of the O-rings 15 will press the biosensor unit 17 against the Peltier elements 16. Then the two Peltier elements will rest against the external surfaces of the reaction chamber 19 in a very good thermal contact. The reaction chamber of the biosensor unit and the Peltier elements will only be separated by the thin foils 23 mentioned above, thereby ensuring excellent heat transfer from the reaction chamber to the Peltier elements.

Although the invention has been described generally with reference to circular or cylindrical geometries of heat sinks, reflectors and housing, circular shapes being favourable for several reasons, it is to be understood that other geometries, such as square, rectangular or other polygon shapes are equally possible, and within the scope of the invention.

The operation and function of a biosensor apparatus will now be given.

The heat developed in the reaction chamber by e.g. an enzyme reaction will give rise to a heat flow from the reaction chamber (hot side) to the heat sinks (cold side). This heat flow will be taken up and dissipated by the heat sinks, and eventually released from them. In order to function as a true biosensor apparatus one characteristic being serial rapid measurements, the design of the heat sinks must be specially adjusted for. This is made possible by selecting the thermal properties (heat capacity, thermal conductivity, emissivity and geometry) of the heat sinks such that they match said characteristic of a biosensor by combining quick absorption of the heat with minimizing the thermal impact from the heat flow on the heat sinks and the environment. In the present arrangement the thermal disturbance is of the order of approx 100 ppm. Due to said features of the heat sinks the heat absorbed by the heat sinks will be released in a time quick enough for the heat sinks to be ready to absorb the next heat flow from the reaction chamber. The heat will be released primarily by radiation and some convection and will in practice not affect the temperature stability of the housing. The thermal properties of the heat sinks should preferably be chosen just as to match the heat flow from the reaction. Because the heat sinks are "thermally insulated" from their immediate environment they will provide for a uniform heat flow being created from the reaction chamber to the heat sinks, in connection with the development of heat in the reaction chamber.

The heat flow gives rise to a temperature gradient across the Peltier elements. By operating the Peltier elements in reverse mode the flow of heat will generate a current from the Peltier elements which is proportional to the heat development in the reaction chamber.

Since the flow of heat from a body is proportional to its area it is advantageous to design the reaction chamber and the Peltier elements in such a way that a maximum contact area is created between them. In one embodiment conventional (flat) square Peltier elements have been employed, with a surface area larger than the area of the reaction chamber, i.e. the surface of the Peltier element should preferably just about cover the reaction chamber. The heat reflectors will act as protective shields, protecting the heat sinks, the Peltier elements and the biosensor unit from incoming sudden changes in heat radiation which in other cases, seriously, might have affected the signal.

In use of the biosensor unit a sample flow is continuously fed through it, and unavoidably some heat from the reaction will escape from the reaction chamber with the outflow. However, by the suggested flat design of the reaction chamber substantially all heat from the reaction will be absorbed by the Peltier elements, and thus only a minute portion will leak out. Thereby a very high efficiency is obtained.

The geometry and area of the biosensor unit with regard to the analyte should be optimized for specific situations. As indicated above the biosensor unit can be designed in many ways, but from a production point of view, a flat configuration is probably preferable.

By virtue of the thermal separation of the heat sinks and reflectors from the environment, the influence by external thermal disturbances will also be reduced. This together with the fact that Peltier elements have a very low impedance, enables a very good signal to noise (S/N) ratio to be achieved. As an example a sample volume of e.g. 1 µl of a glucose solution with the concentration of 4 mmol/l will yield a S/N in one of the present biosensor units of approximately 25:1.

Prior art thermal biosensors have utilized thermistors or thermo-couples as the temperature sensitive elements (transducer) to measure a temperature difference. Besides the complexity (the need for very accurate temperature control system) with temperature difference measurements both of these also have the drawback of a high impedance, and therefore susceptible of picking up noise.

By employing the design principles disclosed above, it is possible to construct a biosensor unit based on thermal flow detection with simplified production Improved usefulness together with a simplified manufacturing process are the main advantages of the present invention.

It should be emphasized that obvious combinations of features of the embodiments described above are within the scope of the invention. The scope of the invention is defined by the appended claims supported by the description and the annexed drawings.

The invention claimed is:

1. A biosensor apparatus comprising:
    a housing (5, 6);
    a pair of heat sinks (11, 12) and a pair of heat reflectors (13, 14) thermally floating relative to the heat sinks, said pairs of heat sinks being arranged in said housing (5, 6) and thermally floating relative to the environment inside the housing (5, 6);
    wherein a space separates each of the pair of heat sinks (11, 12) from each corresponding heat reflector (13, 14); and
    a pair of Peltier elements (16) attached to and in thermal contact with said heat sinks (11, 12), one element (16) on each heat sink (11, 12), there being a gap between them for the accommodation of a generally flat biosensor unit (17) in which reactions can be made to take place, said reactions generating a flow of heat in said heat sinks; wherein
    the housing is made of an insulating and heat radiation resistant material;
    the heat sinks (11, 12) are made of a material with thermal properties selected such that their envelope surfaces have a high heat emissivity, and such that absorption of a heat flow from a reaction in said biosensor can take place within a time of 5-30 seconds, and thereafter the absorbed heat can be released within a time less than 2 min; and wherein
    the heat reflectors (13, 14) have a surface of very low emissivity and a high heat reflectivity, and have a generally flat and thin disc shaped structure.

2. A biosensor apparatus according to claim 1, wherein the heat sinks are made from aluminium or copper.

3. A biosensor apparatus according to claim 1, wherein the reflectors are made from polished aluminium.

4. A biosensor apparatus according to claim 1, wherein the area of said reflector surface of said disc is 1-10 times larger than the facing area of the heat sink.

5. A biosensor apparatus according to claim 1, wherein the Peltier elements (16, 16') are arranged so as to be in a heat conducting contact with thin foils (23) defining opposite walls of a reaction chamber (19) defined by a biosensor unit when the biosensor unit is in an operative position between the Peltier elements (16, $16^5$ J).

6. A biosensor apparatus according to claim 5, wherein the heat conducting contact area between Peltier elements (16, $16^s$) and the foils (23) corresponds to the total reaction chamber wall area defined by said foils (23).

7. A biosensor apparatus according to claim 1, wherein at least one of the Peltier elements (16, $16^5$ J is movable to and from the other Peltier element (16, $16^s$) in order to facilitate insertion of the biosensor unit between the Peltier elements (16, $16^s$).

8. A biosensor apparatus according to claim 1, further comprising snap fitting elements for locking the biosensor unit in its operative position.

9. A biosensor apparatus according to claim 1, wherein the heat sinks (11, 12) are made of the material with thermal properties selected such that their envelope surfaces have a high heat emissivity, and such that absorption of the heat flow from the reaction in said biosensor can take place within a time of 10-20 seconds, and thereafter the absorbed heat can be released within a time less than 1 min.

10. A biosensor apparatus according to claim 1, wherein the heat sinks (11, 12) are made of the material with thermal properties selected such that their envelope surfaces have a high heat emissivity, and such that absorption of the heat flow from the reaction in said biosensor can take place within a time of 10-20 seconds, and thereafter the absorbed heat can be released within a time less than 40 seconds.

11. A biosensor apparatus according to claim 1, wherein the area of said reflector surface of said disc is 3-9 times larger than the facing area of the heat sink.

12. A biosensor apparatus according to claim 1, further comprising a thermally insulating 0-ring located within the space separating each of the pair of heat sinks (11, 12) from each corresponding heat reflector (13, 14).

13. A biosensor apparatus according to claim 1, further comprising low thermal conductivity spacers (26) located within the space separating each of the pair of heat sinks (11, 12) from each corresponding heat reflector (13, 14).

14. A biosensor apparatus according to claim 1, further comprising low thermal conductivity spacers (26) located within the space separating each of the pair of heat sinks (11, 12) from each corresponding heat reflector (13, 14).

15. A biosensor apparatus according to claim 1, further comprising an insulating air gap surrounding the heat sinks and reflectors.

16. A biosensor apparatus according to claim 15, wherein said air gap is about 1 mm.

17. A biosensor apparatus comprising:
    a housing (5, 6);
    a pair of heat sinks (11, 12) and a pair of heat reflectors (13, 14) thermally floating relative to the heat sinks, said pairs of heat sinks being arranged in said housing (5, 6) and thermally floating relative to the environment inside the housing (5, 6), wherein a space separates each of the pair of heat sinks (11, 12) from each corresponding heat reflector (13, 14), and an insulating air gap surrounds the heat sinks and reflectors; and
    a pair of Peltier elements (16) attached to and in thermal contact with said heat sinks (11, 12), one Peltier element (16) on each heat sink (11, 12), there being a gap between the Peltier elements for the accommodation of a generally flat biosensor unit (17) in which reactions can be made to take place, said reactions generating a flow of heat in said heat sinks, wherein,
    the housing is made of an insulating and heat radiation resistant material,
    the heat sinks (11, 12) are made of a material with thermal properties selected such that their envelope surfaces have a high heat emissivity, and such that absorption of a heat flow from a reaction in said biosensor can take place within a time of 5-30 seconds, and thereafter the absorbed heat can be released within a time less than 2 min, and
    the heat reflectors (13, 14) have a surface of very low emissivity and a high heat reflectivity.

* * * * *